United States Patent
Dalgetty et al.

(10) Patent No.: US 7,461,652 B2
(45) Date of Patent: Dec. 9, 2008

(54) IMAGING SYSTEM WITH ANESTHESIA SYSTEM

(75) Inventors: Richard G. Dalgetty, Oakland, CA (US); Brian R. Bates, Lafayette, CA (US); Michael B. Nelson, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 245 days.

(21) Appl. No.: 11/567,386

(22) Filed: Dec. 6, 2006

(65) Prior Publication Data

US 2007/0089742 A1    Apr. 26, 2007

Related U.S. Application Data (62) Division of application No. 10/081,040, filed on Feb. 20, 2002.

(51) Int. Cl.
*A61M 16/00* (2006.01)
*A61M 15/00* (2006.01)

(52) U.S. Cl. .............. 128/203.15; 128/203.12; 128/204.18

(58) Field of Classification Search ............ 128/200.24, 128/203.12, 203.13, 203.14, 203.15, 204.18, 128/204.23; 600/411, 439
See application file for complete search history.

(56) References Cited

U.S. PATENT DOCUMENTS

| | | | |
|---|---|---|---|
| 3,794,027 A | | 2/1974 | Johnson |
| 4,520,808 A | * | 6/1985 | LaBauve ............ 128/200.14 |
| 4,582,055 A | | 4/1986 | McDougal et al. |
| 4,721,060 A | * | 1/1988 | Cannon et al. ............ 119/420 |
| 4,917,046 A | | 4/1990 | Spengler |
| 5,202,091 A | | 4/1993 | Lisenbee |
| 5,297,502 A | * | 3/1994 | Jaeger ............ 119/420 |
| 5,319,209 A | | 6/1994 | Miyakawa et al. |
| 5,414,258 A | | 5/1995 | Liang |
| 5,636,299 A | | 6/1997 | Bueno et al. |
| 5,637,874 A | | 6/1997 | Honzawa et al. |
| 5,650,135 A | | 7/1997 | Contag et al. |

(Continued)

FOREIGN PATENT DOCUMENTS

EP         0 097 060         12/1983

(Continued)

OTHER PUBLICATIONS

Office Action in U.S. Appl. No. 11/567,613 dated Jun. 13, 2007.

(Continued)

*Primary Examiner*—Justine R Yu
*Assistant Examiner*—Annette F Dixon
(74) *Attorney, Agent, or Firm*—Beyer Law Group LLP (57) ABSTRACT

The present invention provides improved anesthesia delivery systems that consistently and reliably deliver anesthesia gas to multiple gas outlets. The systems are particularly useful for anesthetizing multiple mammals and living specimens to be imaged by a low-light level imaging system. The anesthesia delivery systems are suitable for use with conventional oxygen sources, and convert the high pressures associated with a conventional oxygen source to lower pressures suitable for use with small mammals and suitable for combination with an anesthesia gas at low flow rates. The systems include an anesthesia gas source that combines anesthesia gas with the oxygen. The combination of anesthesia gas and oxygen is supplied to one or more multiple outlets.

23 Claims, 6 Drawing Sheets

U.S. PATENT DOCUMENTS

| | | | |
|---|---|---|---|
| 5,705,807 | A | 1/1998 | Throngnumchai et al. |
| 5,738,101 | A | 4/1998 | Sappey |
| 5,840,572 | A | 11/1998 | Copeland et al. |
| 5,867,250 | A | 2/1999 | Baron |
| 5,964,220 | A | 10/1999 | Boussignac et al. |
| 5,970,164 | A | 10/1999 | Bamberger et al. |
| 6,217,847 | B1 | 4/2001 | Contag et al. |
| 6,242,743 | B1 | 6/2001 | DeVito et al. |
| 6,321,111 | B1 | 11/2001 | Perelman et al. |
| 6,352,076 | B1 * | 3/2002 | French ............... 128/203.12 |
| 6,364,829 | B1 | 4/2002 | Fulghum |
| 6,615,063 | B1 | 9/2003 | Ntziachristos et al. |
| 6,775,567 | B2 * | 8/2004 | Cable et al. ............... 600/407 |
| 6,776,158 | B1 * | 8/2004 | Anderson et al. ...... 128/203.12 |
| 6,904,912 | B2 | 6/2005 | Roy et al. |
| 6,992,762 | B2 * | 1/2006 | Long et al. ............... 356/317 |
| 7,164,940 | B2 * | 1/2007 | Hareyama et al. ........... 600/427 |
| 7,213,538 | B2 | 5/2007 | Han et al. |
| 7,252,050 | B2 | 8/2007 | Cole |
| 2007/0089742 | A1 | 4/2007 | Dalgetty et al. |
| 2007/0091428 | A1 | 4/2007 | Wilson et al. |

FOREIGN PATENT DOCUMENTS

| | | |
|---|---|---|
| WO | WO 00/17643 | 3/2000 |

OTHER PUBLICATIONS

Horne, et al., "A Nonrebreathing Anesthetic Delivery System for Mice", Lab Animal Magazine, vol. 27, No. 7, Aug. 4, 1997.

J. B. Mulder, "A Unit for Inhalation Anesthesia of Small Laboratory Animals", Anesthesia and Analgesia, May-Jun. 1973, vol. 52, No. 3, pp. 369-372.

Michael Rand, "Handling, Restraint, and Techniques of Laboratory Rodents", May 2001, Department of Animal Care, University of Arizona.

Hamamatsu Corporation, USA, website, http://usa.hamamatusu.com/ pp. 1-4, Apr. 27, 2001, printed Apr. 27, 2001.

Hamamatsu, Imaging Box Instruction Manual, 55310-224-1, Nov. 2000.

Dosch, Michael P. CRNA MS, "The Anesthesia Gas Machine, Vaporizers, Compressed Gases, Safety:Avoiding the Pitfalls" http://ourworld-top.cs.com/dischm/agmpart1.htm ,http://www.gasnet.org/eduation/machine Copyright. Last revised Aug. 27, 2000.

Smith, Jennifer C., DVM, Brad Bolon, DVM, S, PHD, Diplomate, ACVP, Diplomate, ABT "Atmospheric Waste Isoflurane Concentrations Using Conventional Equipment and Rat Anesthesia Protocols", vol. 41 No. 2, Mar. 2002.

Weigel, Wade "The Intranet in your palm", Penn State Anesthesiology: Anesthesia Scavenging Systems, Mar. 29, 2001, pp. 1-3.

Hamamatsu Corporation, USA, website, http://usa.hamamatusu.com/ pp. 1-2.

Office Action dated Jan. 19, 2006 in U.S. Appl. No. 10/370,031.
Office Action dated Jan. 19, 2006 in U.S. Appl. No. 10/081,040.
Office Action dated May 24, 2006 in U.S. Appl. No. 10/370,031.
Office Action dated May 24, 2006 in U.S. Appl. No. 10/081,040.
Office Action dated May 31, 2007 in U.S. Appl. No. 10/370,031.
Office Action dated Oct. 16, 2006 in U.S. Appl. No. 10/081,040.
Notice of Allowance dated Nov. 28, 2007 in U.S. Appl. No. 10/370,031.
Office Action dated Jan. 7, 2008 in U.S. Appl. No. 10/081,040.
Office Action dated Feb. 21, 2008 in U.S. Appl. No. 11/567,613.
Office Action dated Jul. 2, 2008 from U.S. Appl. No. 10/081,040.
Office Action dated Aug. 15, 2008 from U.S. Appl. No. 11/567,613.

* cited by examiner

IMAGING SYSTEM WITH ANESTHESIA SYSTEM

CROSS-REFERENCE TO RELATED APPLICATIONS

This application claims priority under U.S.C. §120 from co-pending U.S. patent application Ser. No. 10/081,040, filed Feb. 20, 2002 and entitled, "Multiple Output Anesthesia System", which is incorporated herein for all purposes.

FIELD OF THE INVENTION

The present invention relates generally to anesthesia delivery systems. In particular, the present invention relates to anesthesia systems for use with living specimen imaging applications.

BACKGROUND OF THE INVENTION

One new and specialized type of imaging involves the capture of low intensity light—often on the order of only tens to hundreds of photons—from a light-emitting sample. The low intensity light source may be emitted from any of a variety of light-emitting sources within a living specimen, e.g., luciferase expressing cells within a mammalian specimen. The source of the light indicates portions of the sample, such as traced molecules in a particular portion of a laboratory mouse, where an activity of interest may be taking place. Some specialized in-vivo imaging applications may include analysis of one or more representations of emissions from internal portions of a specimen superimposed on a photographic representation of the specimen. The photographic representation provides the user with a pictorial reference of the specimen. The luminescence representation indicates portions of the specimen where an activity of interest may be taking place.

Obtaining the luminescence representation may involve image capture over an extended period of time, e.g., minutes. The living specimen is typically anesthetized during this time to prevent movement that may compromise image capture. Current imaging systems employ anesthesia delivery systems that do not consistently and reliably anesthetize specimens or deliver anesthesia gases. These conventional systems are miniaturized relatives of anesthesia systems used in hospitals and the like. Systems of this nature are designed for a single recipient. However, many imaging systems as described above may require gas delivery to multiple small mammals. So far, scaling to multiple recipients, and via lower flow rates associated with the smaller recipients has been largely unsuccessful.

More specifically, the conventional anesthesia delivery systems rely on a single general upstream flow control for the entire delivery system and downstream on/off switches for each outlet. The result is an anesthesia system that does not reliably deliver gas to each outlet. Commonly, anesthesia gas does not arrive at each interface with a consistent pressure or flow rate. For example, when one outlet is turned on/off, the remaining interconnected outlets do not maintain consistent gas output. As a result, anesthesia gas for one or more of the mammals may be interrupted, fluctuate dramatically—or significantly diminished. Insufficient anesthesia gas supply may result in unintentional consciousness for a mammal, and unexpected locomotion that compromises imaging.

In view of the foregoing, improved anesthesia delivery systems would be desirable.

SUMMARY OF THE INVENTION

The present invention relates to improved anesthesia delivery systems that consistently and reliably deliver anesthesia gas to multiple gas outlets. The systems are particularly useful for anesthetizing multiple mammals and living specimens to be imaged by a low-light level imaging system. The anesthesia delivery systems are suitable for use with conventional oxygen sources, and convert the high pressures associated with a conventional oxygen source to lower pressures suitable for use with small mammals and suitable for combination with an anesthesia gas at low flow rates. The systems include an anesthesia gas source that combines anesthesia gas with the oxygen. The combination of anesthesia gas and oxygen is supplied to one or more multiple outlets.

One outlet of the anesthesia delivery system may lead to an induction chamber used to sedate a living specimen, prior to insertion in an imaging box or chamber. Another outlet may lead to a manifold or gas delivery device having multiple specimen interfaces, each of which is capable providing anesthesia gas to a specimen associated therewith. The manifold or gas delivery device may be placed within the imaging box or chamber and used to maintain a sedated state of the specimen. In one embodiment, the induction chamber includes a scavenger system to collect anesthesia gas that escapes from the induction chamber. In another embodiment, the gas delivery device includes a scavenger system that collects anesthesia gas locally, which is advantageous when the gas delivery device is employed in an imaging box for extended periods.

The present invention may also provide independent control of gases to each of the multiple outlets, thereby enabling reliable gas flow to each gas outlet. This is in contrast to prior art systems comprising general flow control and binary on/off switches for each outlet that do not reliably allow controlled flow to each outlet. In a specific embodiment, the present invention includes a dedicated flowmeter and flow control disposed between an anesthesia source and each gas output.

In one aspect, the present invention relates to a gas delivery system capable of delivering an anesthesia gas to a plurality of gas outlets. The gas delivery comprises an oxygen inlet that receives oxygen from an oxygen source. The gas delivery system also comprises a pressure regulator having an inlet that receives oxygen from the oxygen inlet and having an outlet that provides oxygen at a lower pressure. The gas delivery system further comprises an anesthesia gas source having an inlet coupled to receive low-pressure oxygen from the outlet of the pressure regulator and capable of adding anesthesia gas to the low-pressure oxygen. The gas delivery also comprises a first gas delivery outlet coupled to a gas delivery device having one or more living specimen interfaces and capable of providing anesthesia gas and oxygen to the one or more living specimen interfaces. The gas delivery further comprises a second gas delivery outlet coupled to an induction chamber and capable of providing anesthesia gas and oxygen to the induction chamber.

In another aspect, the present invention relates to an imaging system for capturing an image of a living specimen with a camera. The imaging system comprises an imaging box having a set of walls enclosing an interior cavity and a camera mount configured to position the camera relative the interior cavity. The imaging system also comprises a gas delivery system. The gas delivery system comprises an oxygen inlet that receives oxygen from an oxygen source. The gas delivery system further comprises a pressure regulator having an inlet that receives oxygen from the oxygen inlet and having an outlet that supplies oxygen at a lower pressure. The gas delivery system additionally comprises an anesthesia gas source having an inlet coupled to receive low pressure oxygen from the outlet of the pressure regulator and capable of adding anesthesia gas to the low pressure oxygen. The gas delivery system comprises also a first gas delivery outlet coupled to a gas delivery device that may be placed in the imaging box interior cavity, the gas delivery device having one or more living specimen interfaces and capable of providing anesthesia gas and oxygen to the one or more living specimen interfaces. The gas delivery system further comprises a second gas delivery outlet coupled to an induction chamber and capable of providing anesthesia gas and oxygen to the induction chamber.

In yet another aspect, the present invention relates to a gas delivery device capable of providing anesthesia gas and oxygen to multiple living specimens. The gas delivery device comprises an inlet for receiving anesthesia gas and oxygen, multiple specimen interfaces, and at least one channel for communicating anesthesia gas and oxygen between the inlet and the multiple specimen interfaces. The at least one channel comprises a buffer volume capable of substantially reducing flow rate fluctuations from the multiple specimen interfaces.

In still another aspect, the present invention relates to an induction chamber capable of providing anesthesia gas to a living specimen. The induction chamber comprises a set of walls defining an induction chamber interior. The set of walls include a movable wall that is movable between an opened condition that enables access to the interior, and a closed condition that positions the movable wall to prevent access through the opening and that seals the induction chamber interior from gaseous communication with the environment exterior to the induction chamber. The induction chamber also comprises a gas inlet capable of receiving anesthesia gas and providing the anesthesia gas to the interior of the chamber. The induction chamber further comprises a scavenging system comprising a skirt affixed to the set of walls. The skirt includes a set of holes disposed outside the induction chamber interior. The set of holes are capable of collecting anesthesia gas outside the induction chamber when a suitable negative pressure is applied thereto.

In another aspect, the present invention relates to an imaging system for capturing an image of a living specimen with a camera. The imaging system comprises an imaging box having a set of walls enclosing an interior cavity and a camera mount configured to position the camera relative the interior cavity. The imaging system also comprises a gas delivery system. The gas delivery system includes an oxygen inlet that receives oxygen from an oxygen source and an anesthesia gas source having an inlet coupled to receive oxygen and capable of adding anesthesia gas to the oxygen. The gas delivery system also includes a gas delivery outlet coupled to a gas delivery device that may be placed in the imaging box interior cavity. The gas delivery device has one or more living specimen interfaces and is capable of providing anesthesia gas and oxygen to the one or more living specimen interfaces when in the imaging box interior cavity. The gas delivery device also includes a scavenger system capable of drawing in anesthesia gas output from one or more of the specimen interfaces. The scavenger system comprises an exhaust port for coupling to a conduit, at least one hole capable of drawing in anesthesia gas when a suitable negative pressure is applied thereto, and at least one channel capable of communicating gases between the at least one hole and the exhaust conduit.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

I. Imaging System

Figure 1:
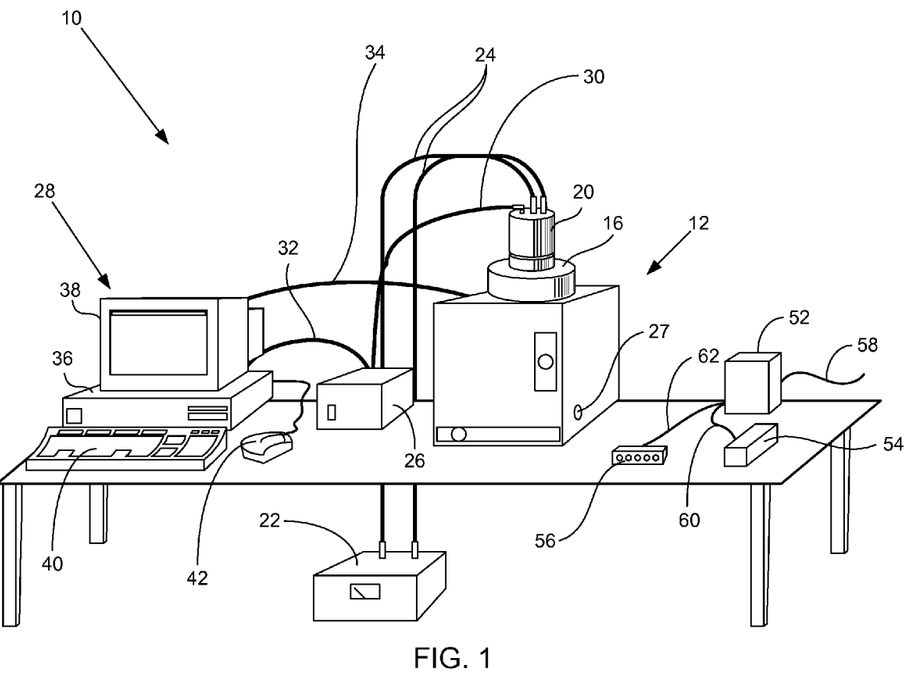
FIG. 1 is a perspective view of an imaging system in accordance with one embodiment of the present invention.

In one aspect, the present invention relates to imaging systems for capturing an image of a low intensity light source. FIG. 1 illustrates an imaging system 10 configured to capture photographic and luminescence images in accordance with one embodiment of the present invention. Imaging system 10 may be used for imaging a low intensity light source, such as luminescence from luciferase-expressing cells, fluorescence from fluorescing molecules, and the like. The low intensity light source may be emitted from any of a variety of light-emitting samples which may include, for example, animals containing light-emitting molecules, e.g., various mammalian subjects such as mice containing luciferase expressing cells.

Imaging system 10 comprises an imaging box 12 having a door and walls that define an interior cavity that is adapted to receive a light-emitting sample in which low intensity light, e.g., luciferase-based luminescence, is to be detected. Imaging box 12 is often referred to as "light-tight", e.g., it seals out essentially all of the external light from the ambient room from entering the box 12, and may include one or more seals that prevent light passage into the box when the door is closed. The seals may also be effective to prevent anesthesia gases used within box 12 from escaping into the ambient room. Imaging box 12 is suitable for imaging including the capture of low intensity light on the order of individual photons, for example.

Imaging box 12 includes an upper housing 16 adapted to receive a camera. A high sensitivity camera 20, e.g., an intensified or a charge-coupled device (CCD) camera, is mounted on top of upper housing 16 and positioned above imaging box 12. CCD camera 20 is capable of capturing luminescent and photographic (i.e., reflection based images) images of a sample placed within imaging box 12. CCD camera 20 is cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other methods, such as liquid nitrogen, may be used to cool CCD camera 20.

Imaging system 10 also includes an anesthesia delivery system (FIGS. 2-5). The anesthesia delivery system includes console 52 (FIGS. 3A and 3B), induction chamber 54 (FIG. 4), and a gas delivery device 56 (FIGS. 5A and 5B). Gas delivery device 56 may be placed within box 12 and includes multiple specimen interfaces for communicating anesthesia gas to one or more living specimens. For example, box 12 typically includes a stage that supports one or more specimens to be imaged, and gas delivery device 56 may be place on the stage in proximity to the living specimens. Conduit 62 allows gaseous communication between gas delivery device 56 and console 52. A light-sealed hole 27 is included in a side wall of box 12 to allow a gas conduit 62 to pass therethrough while device 56 is in box 12. Conduit 62 may comprise tubing or a suitable hose. For example, ⅜ inch OD ¼ inch ID 90 durometer viton rubber tubing is suitable for use as conduit 62.

Oxygen delivery conduit 58, such as a rubber tube or hose, is operably coupled to an oxygen inlet of main console 52 and an outlet of an oxygen supply source. For example, the oxygen supply source may be a high pressure oxygen cylinder or conventional medium pressure wall outlet. Conduits 60 and 62 are coupled to outlets of main console 52 and coupled to inlet of induction chamber 54 and gas delivery device 56, respectively.

An image-processing unit 26 optionally interfaces between camera 20 and a computer 28 through cables 30 and 32 respectively. Computer 28, which may be of any suitable type, comprises a main unit 36 that typically contains hardware including a processor, memory components such as random-access memory (RAM) and read-only memory (ROM), and disk drive components (e.g., hard drive, CD, floppy drive, etc.). Computer 28 also includes a display 38 and input devices such as a keyboard 40 and input mouse 42. Computer 28 is in communication with various components in imaging box 12 via cable 34. To provide communication and control for these components, computer 28 includes suitable processing hardware and software configured to provide output for controlling any of the devices in imaging box 12. The processing hardware and software may include an I/O card, control logic for controlling any of the components of imaging system 10, and a suitable graphical user interface that facilitates user interaction with imaging system 10. Components controlled by computer 28 may include camera 20, motors responsible for camera 20 focus, motors responsible for position control of a platform supporting the living specimens, the camera lens, f-stop, etc.

Computer 28 may also include suitable processing hardware and software for camera 20 such as additional imaging hardware and software, calibration software, and image processing logic for processing information obtained by camera 20. The logic in computer 28 may take the form of software, hardware or a combination thereof. Computer 28 also communicates with a display 38 for presenting imaging information to the user. For example, the display 38 may be a monitor, which presents an image measurement graphical user interface (GUI) that allows a user to view imaging results and also acts an interface to control the imaging system 10.

II. Anesthesia Delivery System

The present invention employs an anesthesia delivery system that reliably delivers anesthesia gases and oxygen to multiple gas outlets. FIGS. 2-5 illustrate different components of an anesthesia delivery system 50 in accordance with one embodiment of the present invention.

Figure 2:
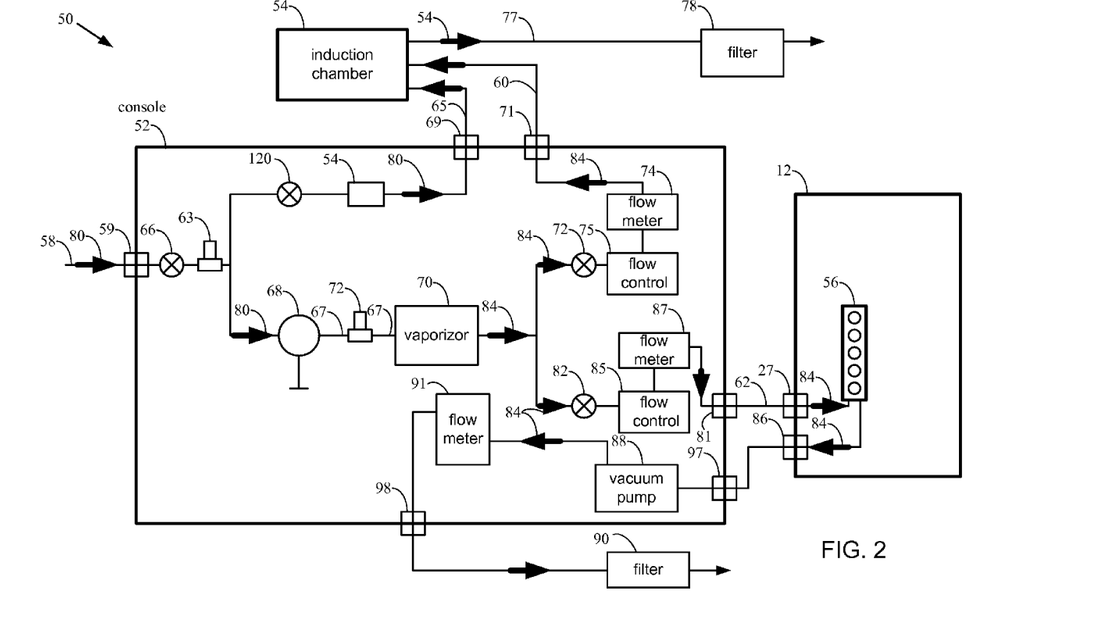
FIG. 2 shows an exemplary functional illustration of an anesthesia delivery system in accordance with one embodiment of the present invention.

FIG. 2 shows an exemplary functional illustration of anesthesia delivery system 50 in accordance with a specific embodiment of the present invention. For illustrative purposes, working-pressure oxygen flow arrows 80 and combined anesthesia gas and oxygen flow arrows 84 are provided to help illustrate the flow of gases through system 50 when all control valves are open and gases flow freely.

Oxygen delivery conduit 58 is coupled to an oxygen inlet 59 of console 52. Oxygen conduit 58 delivers oxygen at a pressure determined by the outlet pressure of an oxygen source that conduit 58 is coupled to. For example, if the oxygen source corresponds to a wall supply, oxygen pressure in conduit 58 is typically between about 45 and about 55 psi. Alternately, if a pressurized cylinder is used as the oxygen source, oxygen pressure is supplied according to the outlet pressure of the tank (up to 2000 psi). Within system 50, oxygen may perform one or more of the following tasks: act as a carrier for an anesthesia gas, life sustainment for a specimen associated with the anesthesia delivery system, a purge gas for induction chamber 54, and a meter for flowmeter measurement. The oxygen inlet 59 of main console 52 includes oxygen on/off valve 66, which allows a user to turn on/off oxygen provided by conduit 58. Oxygen passed through oxygen on/off valve 66 flows to relief valve 63, which limits the pressure seen in system 50 despite the oxygen source outlet pressure. In a specific embodiment, pressure relief valve 63 releases from about 55 to about 95 psi, however, it is understood that the relief pressure of pressure relief valve 63 may adjusted accordingly to the requirements of system 50. From relief valve 63, oxygen flows to purge valve 120 and/or pressure regulator 68.

Pressure regulator 68 includes an inlet that receives oxygen from oxygen inlet 59. Pressure regulator 68 reduces the pressure of oxygen as received at its inlet, and outputs oxygen from a regulator outlet with a lower pressure. In one embodiment, pressure regulator 68 outputs oxygen in the range of about 0.5 to about 5 psi gauge. In a specific embodiment, pressure regulator 68 outputs oxygen at about 1 psi gauge. A pressure regulator model number 8286 as provided by Porter Instruments of Hatfield, Pa. may be suitable for use as pressure regulator 68.

Oxygen output from pressure regular 68 travels via conduit 67 to vaporizer 70. Disposed between pressure regulator 68 and vaporizer 70 is a pressure relief valve 72. In some cases, vaporizer 70 may fail if it sees too high a high-pressure. Pressure relief valve 72 thus protects vaporizer 70 from pressure regulator 68 failure and thereby increases safety of the anesthesia delivery system 50 by maximizing the allowable pressure encountered by vaporizer 70. In a specific embodiment, pressure relief valve 72 releases at 5 psi, however, it is understood that the relief pressure of pressure relief valve 72 may adjusted accordingly to design specifics of vaporizer 70.

The present invention includes an anesthesia gas source or similar device that provides a controllable level of an anesthesia gas or agent. As the term is used herein, an anesthesia gas refers to any gas or agent that is used to induce any level of anesthetic state, unconsciousness, lack of awareness, or local or general insensibility to pain for a specimen interacting with gas delivery system 50. Vaporizer 70 is an anesthesia gas source that adds an anesthesia gas to low-pressure oxygen and includes an inlet that receives low-pressure oxygen from an outlet of pressure regulator 68. The output of vaporizer 70 typically comprises a controlled and variable gas mixture of life sustaining gases and anesthetizing gases. In a specific embodiment, vaporizer 70 adds isoflurane to low pressure oxygen received from pressure regulator 68 by passing the oxygen across a vaporizer that evaporates isoflurane. In this case, the low-pressure oxygen acts as a carrier for the anesthesia gas, which is added to the oxygen according to the physical characteristics of the anesthesia liquid and its temperature. Vaporizer 70 may employ one or more variable bypass, flow over, temperature compensated, and/or agent-specific vaporization techniques. Although the present invention will now be described with respect to vaporizer 70 adding only a single anesthesia gas, isoflurane, it is understood that an anesthesia gas source of the present invention may add multiple anesthesia gases, as one of skill in the art will appreciate. A VIP 3100 Calibrated Vaporizor as provided by MDS Matrix of Orchard Park, N.Y. may be suitable for use as vaporizer 70.

The output 84 of vaporizer 70 is a combination of low-pressure oxygen and anesthesia gas. Vaporizer 70 includes one or more output conduits that lead to separate gas delivery outlets, each of which is capable of providing oxygen and anesthesia gas from console 52. As shown, console 52 includes two gas delivery outlets: a first gas delivery outlet 81 for servicing a gas delivery device having specimen interfaces for communicating gases to one or more living specimens, and a second delivery outlet 71 that services induction chamber 54.

Console 52 includes an on/off valve, flow control valve and flowmeter for each gas delivery outlet that delivers oxygen and anesthesia gas from console 52. More specifically, a first on/off valve 72 allows a user to turn on/off low-pressure oxygen and anesthesia gas provided by output port 71. Conduit 60 provides gaseous communication between output port 71 and induction chamber 54. Flow control 75 is disposed between on/off valve 72 and output port 71, and allows a user to variably control and set the flow rate of low-pressure oxygen and anesthesia gas supplied from output port 71. Flowmeter 74 is disposed before output port 71 and after flow control 75 and measures the flow rate of gases that pass there through. In one embodiment, flowmeter 74 includes a conventional output that visually indicates flowrate to a user. After low-pressure oxygen and anesthesia gas pass through on/off valve 72, flow control 75, flowmeter 74, and output port 71, the gases are supplied to induction chamber 54.

Induction chamber 54 receives low-pressure oxygen and anesthesia gas from conduit 73. Induction chamber 54 allows a user to anesthetize a living specimen that fits within induction chamber 54, and will be described in further detail with respect to FIG. 4. An exhaust port 132 (FIG. 4) is included in the side of induction chamber 54 and is coupled to conduit 77. Exhaust port 132 and conduit 77 withdraw gases from induction chamber 54 and provide them to filter 78. In one embodiment, filter 78 is a charcoal filter that removes unused isoflurane that passes therethrough. A filter model number 80120 F/Air Cannister as provided by A.M. Bickford of Wales Center, N.Y. is suitable for use as filter 78. Filter 78 outputs primarily oxygen. As shown, filter 78 outputs oxygen into the ambient room.

Figure 5A:
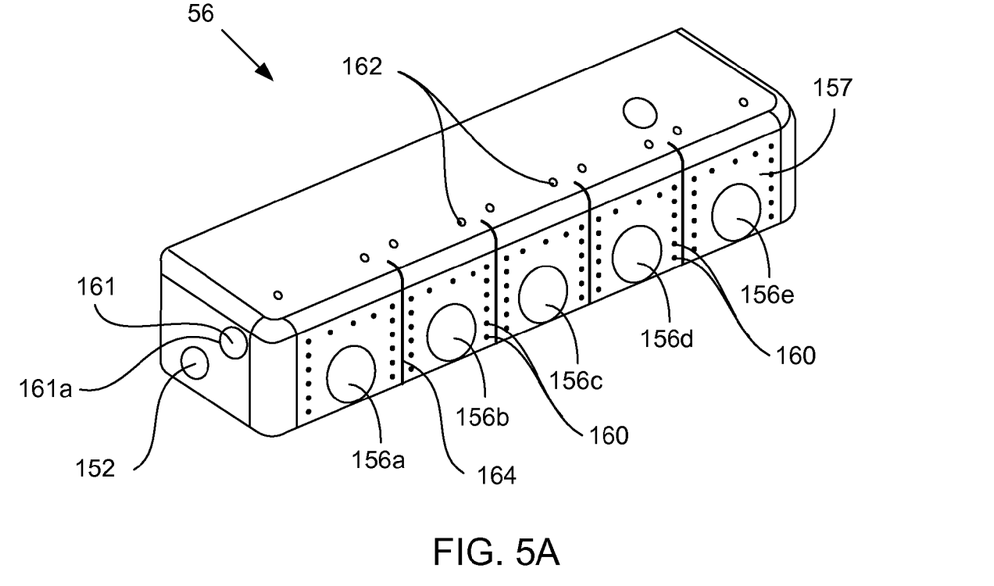
FIG. 5A illustrates a gas delivery device in accordance with one embodiment of the present invention.

Console 52 includes a second outlet that provides oxygen and anesthesia gas supply to gas delivery device 56 (FIG. 5). More specifically, on/off valve 82 allows a user to turn on/off low-pressure oxygen and anesthesia gas provided by output port 81. Conduit 62 provides gaseous communication between output port 81 and gas delivery device 56. Flow control 85 is disposed between on/off valve 82 and output port 81, and allows a user to variably control and set the flow rate of low-pressure oxygen and anesthesia gas supplied from output port 81. Flowmeter 87 is disposed before output port 81 and after flow control 85 and measures the flow rate of gases that pass therethrough. In one embodiment, flowmeter 84 is a conventional mechanical flowmeter, such as a conventional rotometer, and may comprise one or more of the following components: a needle valve, an indicator float, user control knobs, and valve stops. In another embodiment, an electronic flowmeter is employed and flow rate is indicated on a monitor screen or similar electronic output device. After low-pressure oxygen and anesthesia gas pass through on/off valve 82, flow control 85, flowmeter 84, and output port 81, the gases are supplied to gas delivery device 56.

Thus, each gas delivery outlet of system 50 comprises its own flow control. As opposed to conventional anesthesia delivery systems in which anesthesia gas delivery is controlled by a general flow control that roughly adapts the amount of oxygen received from an oxygen supply source, disposing a dedicated flow control and flowmeter for each outlet according to system 50 allows precise and independent control of gases to induction chamber 54 and gas delivery device 56. In particular, system 50 allows independent and specific control of anesthesia gases to each outlet—after generation of the anesthesia gas by vaporizer 70—thereby allowing a user to variably tailor the amount of anesthesia gas provided to a specimen at any given time. In a specific embodiment, flow control 75 comprises a control knob that allows a user to vary flow rate from about 0 L/min to about 5 L/min through outlet port 71. In another specific embodiment, flowmeter 85 comprises a control knob that allows a user to vary flow rate from about 0 L/min to about 2 L/min through outlet port 81.

Gas delivery device 56 receives low-pressure oxygen and anesthesia gas from conduit 62. Gas delivery device 56, which will be described in further detail with respect to FIG. 5, includes a number of specimen interfaces, each of which is capable of accommodating a living specimen and providing oxygen and anesthesia gas to the specimen. The anesthesia gas may be used to anesthetize a living specimen, or if the specimen is already anesthetized—to maintain a desired anesthetic state.

Anesthesia gas introduced into imaging box 12 via gas delivery device 56 may be collected and exhausted to alleviate the buildup of anesthesia gases in the box. Imaging box 12 includes a sealed exhaust port 86 that allows collected anesthesia gases to be removed from within imaging box 12. Conduit 95 is coupled on its opposite ends to exhaust port 86 and vacuum port 97, which leads to a vacuum pump 88. Vacuum pump 88 applies a negative pressure through conduit 95 sufficient to draw anesthesia gases from within box 12. In one embodiment, vacuum pump 88 draws and collects anesthesia gases generally from the box 12 interior. In another embodiment, gas delivery device 56 includes a scavenging system that locally removes gases introduced by the specimen interface and not used by one or more living specimens (explained in greater detail with respect to FIG. 5). Either way, vacuum pump 88 and conduit 95 collect unused anesthesia gases from box 12. Flowmeter 91 allows a user to determine the flow rate of gases drawn through vacuum pump 88. In another embodiment, a suitable flow control is employed to allow a user to set the pressure/flow rate of gases drawn by pump 88. Gases collected by pump 88 are then transmitted to filter 90 through an outlet port 98 of console 52. In one embodiment, filter 90 is a charcoal filter that removes unused isoflurane and outputs primarily oxygen enriched air into the ambient room.

Figure 3A:
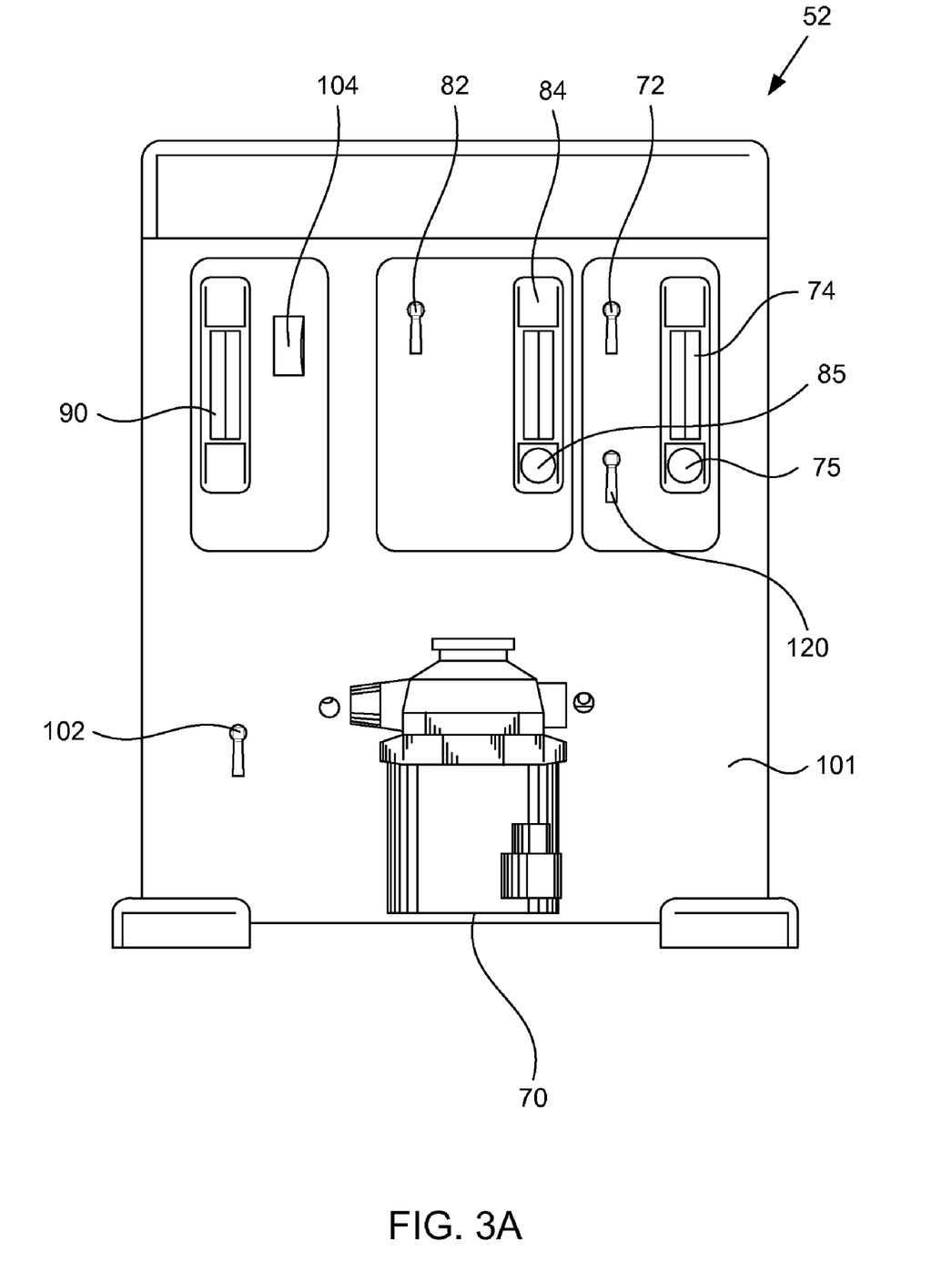
FIGS. 3A and 3B illustrate front and rear views, respectively, of an exemplary anesthesia delivery console in accordance with one embodiment of the present invention.
Figure 3B:
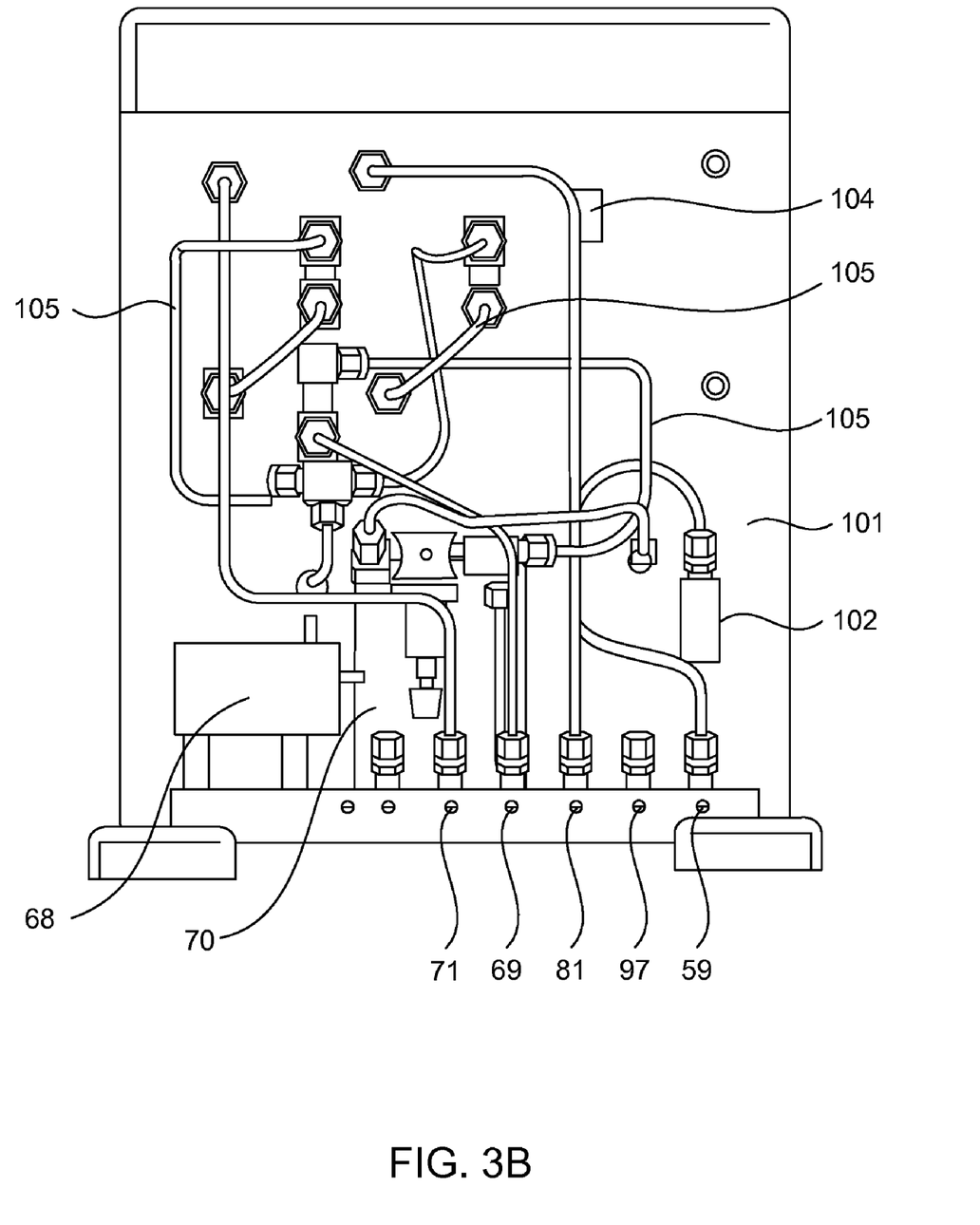

FIGS. 3A and 3B illustrate front and back views, respectively, of console 52 in accordance with one embodiment of the present invention. As shown, a housing 101 supports many of the components described with respect to FIG. 2 as well as numerous other interface mechanisms. For example, switch 102 (FIG. 3A) permits control of oxygen on/off valve 66 of FIG. 2. Exhaust pump 88 is controlled using pump on/off switch 104, which is disposed beside flowmeter 91. On/off switches and flowmeters are also illustrated for each of the gas outlets. Referring to FIG. 3B, numerous conduits 105 are shown that interconnect many of the functional components of console 52 and the inlet and outlet ports 59, 69, 71, 81, and 97. In a specific embodiment, ¼ inch OD orbital welded stainless steel tubes are used as conduits 105 and are fixed to their respective ports and components using standard industrial gas fittings. Alternately, ⅜ inch OD 60 durometer viton rubber tubing may be used for conduits with significant bending.

Having briefly discussed the functional arrangement of anesthesia delivery system 50 in accordance with one embodiment of the present invention, several gas delivery components of the system will now be described in further detail.

III. Induction Chamber

Figure 4:
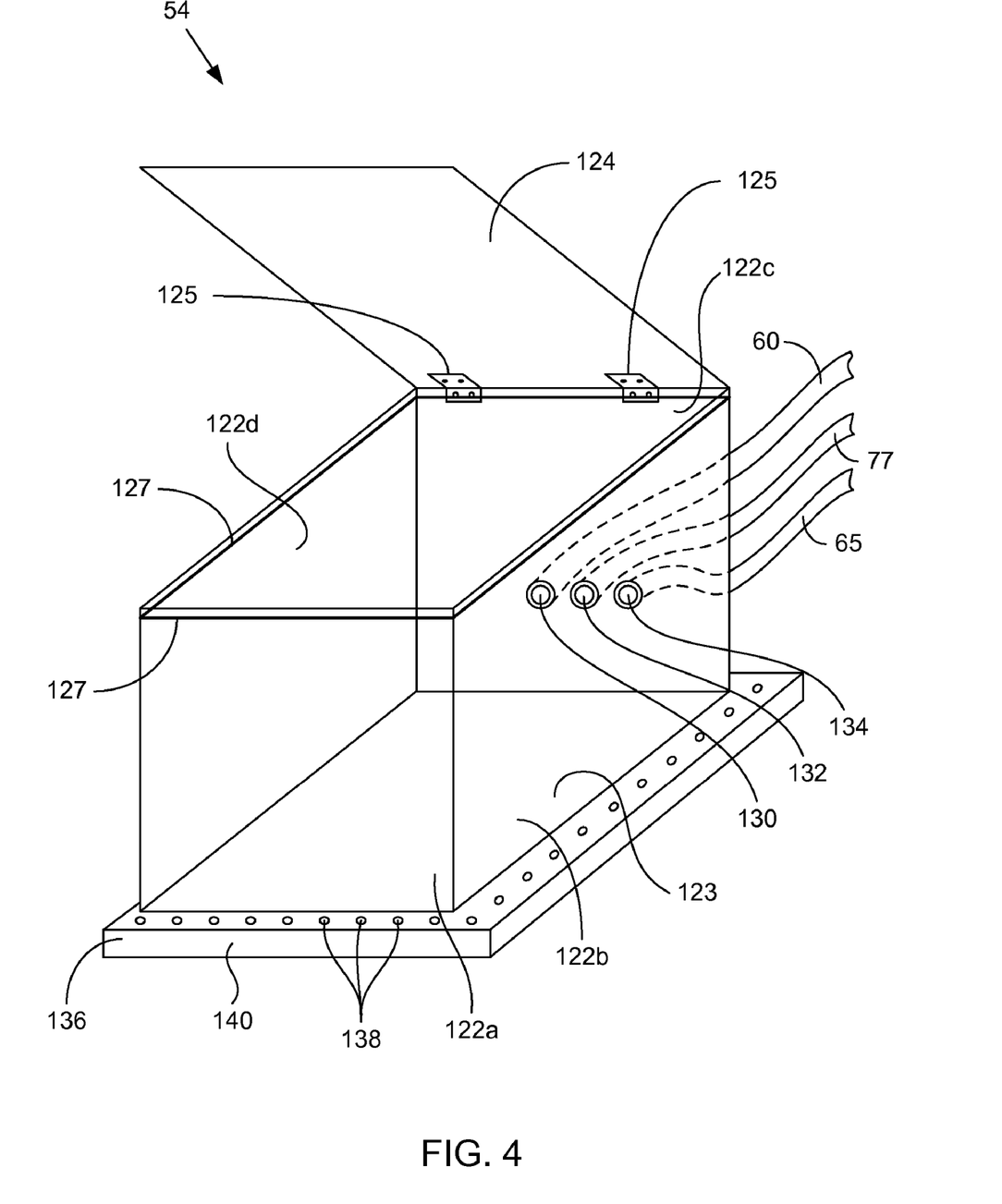
FIG. 4 illustrates an induction chamber in accordance with one embodiment of the present invention.

FIG. 4 illustrates induction chamber 54 in accordance with one embodiment of the present invention. Induction chamber 54 allows a user to anesthetize a living specimen that fits within induction chamber 54. As shown, induction chamber 54 includes four vertical walls 122a-d fixed to a bottom 123. Lid 124 is hingeably coupled to back wall 122c using hinges 125 that are fixed to the outer sides of wall 122c and lid 124. Walls 122, bottom 123 and lid 124 define an interior of induction chamber 54. Lid 124 is movable between an opened condition that defines an opening into chamber 54 and enables access to the interior, and a closed condition that prevents access to the interior. Seal 127 is disposed along the inner surfaces of walls 122 and mates with lid 124, when lid 124 is in the closed position, to provide a seal that prevents gaseous communication between the interior of induction chamber 54 and the environment exterior to induction chamber 54. In a specific embodiment, seal 127 comprises a rubber or silicone seal and walls 122, bottom 123, and lid 124 or all made from a transparent plastic such polycarbonate. Using transparent walls for induction chamber 54 advantageously allows a user to view the interior of induction chamber 54.

Inlet port 130 is disposed in back wall 122c and allows gaseous communication between the inside and outside of induction chamber 54. As shown, inlet port 130 receives conduit 60, which provides low-pressure oxygen and anesthesia gas from port 71 of console 52.

In one embodiment, outlet port 132 is disposed in back wall 122c and allows gaseous communication between the inside and outside of induction chamber 54. As shown, outlet port is coupled to conduit 77, which exhausts gases from induction chamber 54 to filter 78 (FIG. 2). As shown, anesthesia gases are exhausted from induction chamber 54 based on positive pressure build up in the interior and relief using conduit 77. In an active removal embodiment, conduit 77 may be associated with negative pressure via a vacuum pump, such as vacuum pump 88 of FIG. 2, to actively draw gases from induction chamber 54.

In another embodiment, induction chamber 54 employs a scavenging system to collect and exhaust anesthesia gases. After anesthetizing a living specimen within induction chamber 54, a user typically opens lid 124 to move the specimen into imaging box 12. At this point, gases from within the chamber 54 interior—including anesthesia gases—may escape from induction chamber 54. Often, the anesthesia gas is denser than air and spills over the side walls 122. To facilitate the capture of anesthesia gas that escapes from induction chamber 54, the scavenging system employed by induction chamber 54 includes holes 138 disposed in a skirt 140. The top of skirt 140 is attached to bottom 123. Holes 138 are peripherally disposed about walls 122 and associated with channels (not shown) within skirt 140 that collectively lead to an outlet port, or similar interface, that couples to a conduit and vacuum pump 88. Vacuum pump 88 provides a suitable negative pressure that draws gases into holes 138 and creates a downdraft about the outside of induction chamber 54. Thus, anesthesia gases that escape the induction chamber 54 interior may be collected by holes 138, pass through their associated channels, and flow to the vacuum pump for subsequent filtering. In one embodiment, skirt 140 comprises from about 10 to about 50 holes, each having a diameter of about 0.061 to about 2.54 mm. In a specific embodiment, skirt 140 comprises 17 holes, each having a diameter of about 1.86 mm.

Inlet port 134 is also disposed in back wall 122c and allows gaseous communication between the inside and outside of induction chamber 54. Inlet port 134 is coupled to conduit 65, which provides working pressure oxygen communication with purge valve 120. Referring back to FIG. 2, purge valve 120 allows a user to flood induction chamber 54 with working pressure oxygen from the regulated supply pressure oxygen source. Flow restricter 122 reduces the flow rate of oxygen provided by the external oxygen supply before entering induction chamber 54. Conduit 65 is coupled to oxygen induction chamber outlet 69 of console 52 and an oxygen inlet port 134 of induction chamber 54.

In operation, a user opens lid 124 and places a living specimen within the interior of induction chamber 54. After closing lid 124, and sealing the interior of induction chamber 54 from the ambient room, oxygen and anesthesia gas are supplied to the interior via console 52 and inlet port 130. During this time, exhaust gases may be actively removed from induction chamber 54 using a pump or one of the exhaust techniques described above. After anesthesia delivery to the living specimen is complete, e.g. when the specimen has been put to sleep, lid 124 is opened and the specimen removed. Scavenging exhaust 136 may collect and exhaust anesthesia gases that escapes induction chamber 54.

IV. Specimen Interface

The present invention also relates to a gas delivery device that is capable of delivering an anesthesia gas and oxygen to multiple living specimens. FIG. 5A illustrates a top perspective view of gas delivery device 56 of FIG. 1 in accordance with one embodiment of the present invention. Gas delivery device 56 is particularly useful for operation in imaging box 12 to maintain the anesthetic state of a specimen induced by induction chamber 54. Gas delivery device 56 comprises a front face 157 having many features suitable for gas interchange with multiple living specimens. In a specific embodiment, gas delivery device 56 is a solid structure machined from one or more pieces of black anodized aluminum.

Figure 5B:
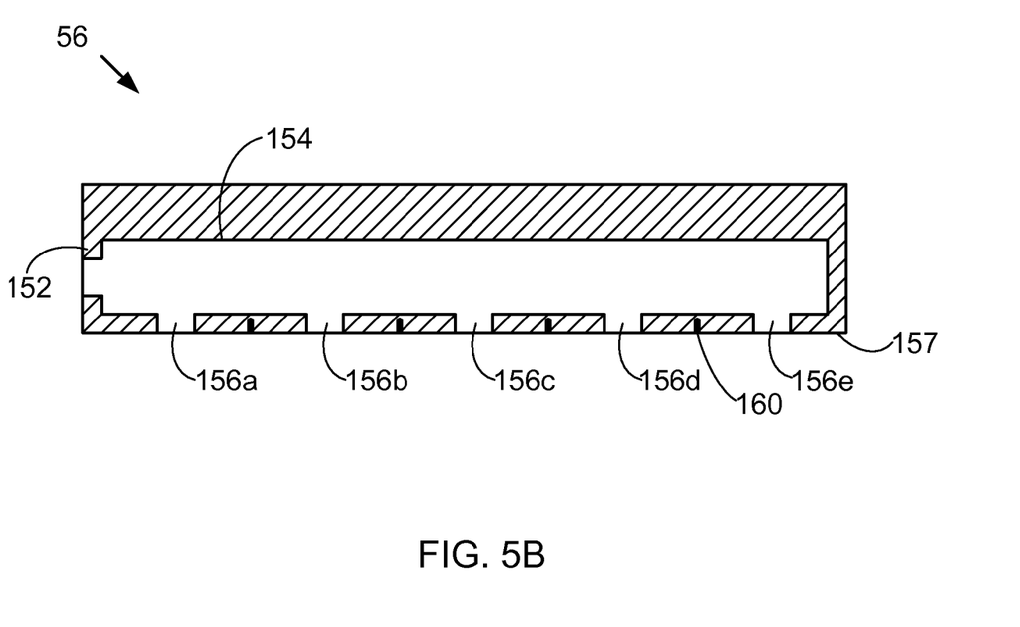
FIG. 5B illustrates a top cutaway view of the gas delivery device of FIG. 5A showing its internal channel taken through the midsection of each specimen interface.

Gas delivery device 56 comprises an inlet port 152 on one end for coupling to a conduit that delivers an anesthesia gas and oxygen, such as conduit 62 from outlet port 81 of console 52. Five specimen interfaces 156a-e are horizontally disposed along a front face 157 of gas delivery device 56. Inlet port 152 opens into a channel 154 (FIG. 5B) that substantially spans the length of device 56. FIG. 5B illustrates a top cutaway view of gas delivery device 56 showing channel 154 taken through the vertical midsection of each specimen interfaces 156. Channel 154 communicates anesthesia gases and oxygen from inlet port 152 to each specimen interface 156.

Channel 154 is larger in cross-sectional area than inlet port 152 includes a buffer volume sufficiently large to substantially reduce flow rate inconsistencies and fluctuations to and from the specimen interfaces 156. In this manner, a large volume of gas accumulated within channel 154 may act as a buffer to facilitate substantially constant flow of anesthesia gas and oxygen from interfaces 156 despite fluctuations in the delivery of anesthesia gas and oxygen. In a specific embodiment, channel 154 is circular in cross-section and has a diameter in the range of about 0.15 to about 0.75 inches and a length spanning device 56 save the outside walls. In a specific embodiment, channel 154 is circular in cross-section and has a diameter of about 0.313 inches.

In one embodiment, a disposable sleeve is inserted each specimen interface 156. The disposable sleeve has a smaller orifice at channel 154 and a larger orifice distal from channel 154 at front face 157. In a specific embodiment, the disposable sleeve includes a substantially frustoconical shape that increases in diameter as it extends away from channel 154. In operation, the head of a specimen is disposed in, or proximate to, the disposable sleeve. When the disposable sleeve is used with a sleeping mouse for example, the head of the mouse may rest on the disposable sleeve. Since the cross-sectional area that the anesthesia gas encounters increases as it travels through the disposable sleeve, the flow rate of the gas decreases as it approaches the specimen. As a result, the anesthesia gas may have a more laminar and less turbulent flow from each specimen interface 156.

Gas delivery device 56 also comprises a scavenger system capable of drawing and collecting waste anesthesia gases. Since the amount of anesthesia gas supplied usually exceeds the amount necessary for the specimen, scavenging according to the present invention decreases box 12 pollution—and pollution in the surrounding room after the door to box 12 is opened.

As shown, the scavenger exhaust comprises an array of holes 160 perimetrically located about each of the specimen interfaces 156. Holes 160 locally draw and collect anesthesia gas when a suitable negative pressure is applied thereto. An exhaust port 161 acts as an exterior outlet from gas delivery device 56 and allows external attachment to a conduit. A longitudinal channel (not shown) allows gaseous communication between exhaust port 161 and each of the holes 160. The longitudinal channel runs the face 157 length of gas delivery device 56 from exhaust port 161 to the opposite end. Internal channels (not shown) extend within gas delivery device 56 between each of the holes 160 and the longitudinal channel. In one embodiment, a conduit connected to exhaust port 161 actively draws gases through holes 160, through their associated internal channels, through the longitudinal channel, and through exhaust port 161 using a negative pressure, e.g. via a pump such as pump 88. Holes 160 are particularly useful for drawing in anesthesia gas output towards a specimen by the specimen interfaces 156. In one embodiment, oxygen and anesthesia gases flow from each specimen interface 156 is supplied in a laminar and substantially non-turbulent manner. Holes 161 may then locally draw anesthesia gas in a minimally turbulent manner; thereby minimizing gas escape into imaging box 12.

In another embodiment, holes 162 are also disposed in the upper surface of gas delivery device 56 to capture anesthesia gas not locally captured by holes 161 and to capture anesthesia gas above gas delivery device 56. Internal channels (also not shown) extend from holes 162 downward towards the longitudinal channel and deliver collected gases to exhaust port 161.

When imaging is performed on multiple living specimens using gas delivery device 56, it may be desirable to prevent light emitted by one specimen from reaching an adjacent specimen. To this end, gas delivery interface also includes a vertical slot 164 disposed between each of the adjacent specimen interfaces 156. Each vertical slot 164 is capable of receiving and vertically holding a light barrier, such as a paper or otherwise suitable opaque barrier. In a specific embodiment, each vertical slot 164 is between 0.03 and 0.04 inches thick and penetrates ¼ inch into face 157.

While this invention has been described in terms of several preferred embodiments, there are alterations, permutations, and equivalents which fall within the scope of this invention which have been omitted for brevity's sake. For example, although gas delivery device 56 is described as a solid structure machined from aluminum, it is understood that other designs may the structure of the gas delivery device and include tube and bellows systems that equally deliver anesthesia gas to multiple living specimens. It is therefore intended that the scope of the invention should be determined with reference to the appended claims.

What is claimed is:

1. An imaging system for capturing an image of a living specimen with a camera, the system comprising:
    an imaging box configured to simultaneously image multiple specimens in the imaging box with light, the imaging box having a door and set of walls enclosing an interior cavity; and
    a gas delivery system comprising:
        an oxygen inlet that receives oxygen from an oxygen source,
        an anesthesia gas source configured to add anesthesia gas to the oxygen, and
        a gas delivery outlet coupled to a gas delivery device configured to be placed in the imaging box interior cavity, the gas delivery device having multiple living specimen interfaces and configured to provide anesthesia gas and oxygen to the multiple living specimens when in the imaging box interior cavity.

2. The gas delivery system of claim 1 wherein the gas delivery outlet comprises an outlet port and a flow control disposed between the anesthesia gas source and the outlet port.

3. The gas delivery system of claim 2 wherein the flow control allows control of gases from about 0 L/min to about 5 L/min to the gas delivery outlet.

4. The gas delivery system of claim 1 wherein the gas delivery system includes a second gas delivery outlet coupled to an induction chamber and capable of providing anesthesia gas and oxygen to the induction chamber.

5. The gas delivery system of claim 4 wherein the second gas delivery outlet comprises an outlet port and a second flow control disposed between the anesthesia gas source and the outlet port.

6. The gas delivery system of claim 1 wherein the gas delivery device further comprises an inlet for receiving anesthesia gas and oxygen and at least one channel configured to communicate anesthesia gas and oxygen between the inlet and the multiple specimen interfaces.

7. The gas delivery system of claim 6 wherein the at least one channel comprises a buffer volume sufficiently large to substantially reduce flow rate fluctuations from the multiple specimen interfaces.

8. The gas delivery system of claim 1 further comprising a pressure regulator having an inlet that receives oxygen from the oxygen inlet and having an outlet that provides oxygen at a lower pressure.

9. The gas delivery system of claim 1 wherein each of the multiple living specimen interfaces provide a substantially equal flow relative to each other.

10. An imaging system for capturing an image of a living specimen with a camera, the system comprising:
   an imaging box configured to simultaneously image multiple specimens in the imaging box with light, the imaging box having a door and set of walls enclosing an interior cavity and a camera mount configured to position the camera relative the interior cavity; and
   a gas delivery system including;
      an oxygen inlet that receives oxygen from an oxygen source;
      an anesthesia gas source having an inlet coupled to receive oxygen and capable of adding anesthesia gas to the oxygen; and
   a gas delivery outlet coupled to a gas delivery device that may be placed in the imaging box interior cavity, the gas delivery device having multiple living specimen interfaces and configured to provide anesthesia gas and oxygen to the multiple living specimens when in the imaging box interior cavity, the gas delivery device also including a scavenger system capable of drawing in anesthesia gas output from one or more of the specimen interfaces, the scavenger system comprising an exhaust port for coupling to a conduit, at least one hole capable of drawing in anesthesia gas when a suitable negative pressure is applied thereto, and at least one channel capable of communicating gases between the at least one hole and the exhaust conduit.

11. The gas delivery system of claim 10 wherein the gas delivery system includes a second gas delivery outlet coupled to an induction chamber and capable of providing anesthesia gas and oxygen to the induction chamber.

12. The gas delivery system of claim 10 wherein the at least one channel comprises a buffer volume sufficiently large to substantially reduce flow rate fluctuations from the multiple specimen interfaces.

13. The gas delivery system of claim 10 further comprising a disposable sleeve inserted within a specimen interface, the disposable sleeve having a smaller orifice at the at least one channel and a larger orifice distal from the at least one channel.

14. The gas delivery system of claim 10 wherein each of the multiple living specimen interfaces provide a substantially equal flow relative to each other.

15. An imaging system for capturing an image of a living specimen with a camera, the system comprising:
   an imaging box configured to simultaneously image multiple specimens in the imaging box with light, the imaging box having a door and set of walls enclosing an interior cavity; and
   a gas delivery system comprising;
      an oxygen inlet that receives oxygen from an oxygen source;
      a pressure regulator having an inlet that receives oxygen from the oxygen inlet and having an outlet that provides oxygen at a lower pressure;
      an anesthesia gas source having an inlet coupled to receive low pressure oxygen from the outlet of the pressure regulator and capable of adding anesthesia gas to the low pressure oxygen;
      a first gas delivery outlet coupled to a gas delivery device that may be placed in the imaging box interior cavity, the gas delivery device having multiple living specimen interfaces and configured to provide anesthesia gas and oxygen to the multiple living specimens when in the imaging box interior cavity; and
      a second gas delivery outlet coupled to an induction chamber and capable of providing anesthesia gas and oxygen to the induction chamber.

16. The imaging system of claim 15 wherein the first gas delivery outlet comprises an outlet port and a first flow control disposed between the anesthesia gas source and the outlet port.

17. The imaging system of claim 16 wherein the second gas delivery outlet comprises an outlet port and a second flow control disposed between the anesthesia gas source and the outlet port.

18. The imaging system of claim 17 wherein the first and second flow control each allow independent flow control of gases to the first gas delivery outlet and to the second gas delivery outlet.

19. The imaging system of claim 18 wherein the first flow control allows control of gases from about 0 L/min to about 5 L/min to the first gas delivery outlet.

20. The imaging system of claim 15 wherein the induction chamber further comprises a gas scavenging system that collects anesthesia gas and oxygen that escape from the induction chamber interior.

21. The imaging system of claim 15 further comprising a purge inlet capable of providing oxygen to the induction chamber interior.

22. The imaging system of claim 15 wherein the gas delivery device further comprises an inlet for receiving anesthesia gas and oxygen and at least one channel for communicating anesthesia gas and oxygen between the inlet and the multiple specimen interfaces.

23. The imaging system of claim 22 wherein the at least one channel comprises a buffer volume sufficiently large to substantially reduce flow rate fluctuations from the multiple specimen interfaces.

* * * * *